United States Patent [19]

Beschke et al.

[11] 4,149,002

[45] Apr. 10, 1979

[54] PROCESS FOR THE PRODUCTION OF 2-METHYL PYRIDINE AND 3-METHYL PYRIDINE

[75] Inventors: Helmut Beschke; Heinz Friedrich, both of Hanau, Fed. Rep. of Germany

[73] Assignee: Deutsche Gold- und Silber Scheideanstalt vormals Roessler, Frankfurt, Fed. Rep. of Germany

[21] Appl. No.: 871,978

[22] Filed: Jan. 24, 1978

[30] Foreign Application Priority Data

Jan. 26, 1977 [DE] Fed. Rep. of Germany ....... 2703069

[51] Int. Cl.$^2$ .......................................... C07D 213/12
[52] U.S. Cl. .................................................. 546/251
[58] Field of Search ...................................... 260/290 P

[56] References Cited

FOREIGN PATENT DOCUMENTS 920526  3/1963  United Kingdom ................. 260/290 P

OTHER PUBLICATIONS

Emmett, Catalysis, vol. 7, pp. 6–9, Reinhold Pub., 1960.

*Primary Examiner*—Alan L. Rotman
*Attorney, Agent, or Firm*—Cushman, Darby & Cushman

[57] ABSTRACT

2-Methyl pyridine and 3-methyl pyridine are produced by the catalytic reaction of acrolein and acetone with ammonia in the gas phase. There is used as the catalyst a highly dispersed aluminum silicate containing 3 to 30 weight percent aluminum oxide, a BET surface area of 200 to 800 m$^2$/g, a pore volume of 0.4 to 1.0 cm$^3$/g and a pore diameter of 20 to 100 × 10$^{-8}$ cm.

19 Claims, No Drawings

PROCESS FOR THE PRODUCTION OF 2-METHYL PYRIDINE AND 3-METHYL PYRIDINE

BACKGROUND OF THE INVENTION

The present invention is directed to a process for the production of 2-methyl pyridine and 3-methyl pyridine by the catalytic reaction of acrolein and acetone with ammonia in the gas phase.

It is known that 2-methyl pyridine and 3-methyl pyridine are formed by the reaction of acrolein and acetone with ammonia in the gas phase in the presence of catalysts. As catalysts there are used aluminum oxide, silica or silica in admixture with 5 to 50% of aluminum oxide, in a given case with the addition of oxides of additional elements (Hargreave, British Pat. No. 920,526). In this process the combined yield of 2-methyl pyridine and 3-methyl pyridine is only 38% (Hargreave Example 2). In that example the silica and alumina are modified by lead.

SUMMARY OF THE INVENTION

There has now been found a process for the production of 2-methyl pyridine and 3-methyl pyridine by catalytic reaction of acrolein and acetone with ammonia in the gas phase which is characterized by using as the catalyst highly dispersed aluminum silicate which contains 3 to 30 weight percent aluminum oxide, a BET surface area of 200 to 800 m$^2$/g, a pore volume of 0.4 to 1.0 cm$^3$/g and a pore diameter of 20 to 100 $\times 10^{-8}$ cm (20 to 100 A). With this process there are produced considerably higher yields than in the known process. Also the space-time-yields are substantially better.

The aluminum silicates used according to the invention preferably have an aluminum oxide content of 5 to 20% and especially from 10 to 15%. They preferably have a BET surface area of 300 to 600 m$^2$/g, a pore volume of 0.6 to 0.8 cm$^3$/g, a pore volume of 0.6 to 0.8 cm$^3$/g and a pore diameter of 40 to 80$\times 10^{-8}$ cm.

The aluminum silicates can be made in known manner, for example, by treating an aqueous sodium silicate solution with sulfuric acid and mixing the silica gel produced with aluminum sulfate and ammonia, separating and freeing of the aluminum silicate from foreign ions, drying and tempering (Paul H. Emmett, Catalysis, Vol. VII, Reinhold Publishing Corp., especially pages 5 to 9). The entire disclosure of Emmett is hereby incorporated by reference and relied upon.

To carry out the process of the invention acrolein, acetone and ammonia are added in customary manner in gaseous form. The molar proportions can be chosen substantially at random. However, it is generally suitable per mole of acrolein to use about 0.1 to 2.5 moles, preferably 0.2 to 2.0 moles, especially 0.5 to 1.5 moles of acetone. Besides it is generally suitable to add per mole of oxo compound (acrolein and acetone) at least about 1 mole of ammonia. It is advantageous to use per mole of oxo compound about 1.0 to 3.0 moles, especially 1.3 to 2.5 moles, of ammonia. Suitably there is introduced additionally an inert gas, especially nitrogen, that is, advantageously per mole of oxo compound 0.5 to 3.0 moles, particularly 1.0 to 2.5 moles of inert gas.

The molar ratio of acetone to acrolein is, in a given case, to a certain extent dependent upon whether it is desired to favor the formation of 2-methyl pyridine or 3-methyl pyridine. The greater the molar ratio of acetone to acrolein the greater is the portion of 2-methyl pyridine.

The catalyst is used in a fixed bed, generally in a particle size of 0.2 to 3.0 mm, especially of 0.5 to 2.0 mm, or preferably in a fluidized bed, generally in a particle size of 0.1 to 3.0 mm, especially of 0.2 to 2.0 mm. Advantageously the aldehydes are fed into the reaction space separately from the ammonia. Particularly, there is chosen for this purpose the procedure of German OS No. 2,449,340 or corresponding Beschke U.S. application Ser. No. 622,488 filed Oct. 15, 1975, however, with the difference that instead of acrolein in each case there is added a mixture of acrolein and acetone. There are hereby incorporated by reference and relied upon the entire disclosure of German OS No. 2,449,340 and Beschke U.S. application Ser. No. 622,488.

The reaction takes place at temperatures between about 300° and 500° C., especially between 380° and 480° C. The pressure can be chosen substantially at random, however, it is recommended so that a simple apparatus can be used to operate at normal pressure or only moderately lowered or elevated pressure up to about 3 bar. A slight under pressure or over pressure results in a given case in that the gases are sucked through the plant or forced through by pressure.

The process can comprise, consist essentially of or consist of the steps set forth and the material employed can comprise, consist essentially of or consist of those set forth.

Unless otherwise indicated all parts and percentages are by weight.

DESCRIPTION OF THE PREFERRED EMBODIMENTS

EXAMPLE 1

There was used a fluidized bed reactor. This consisted of a tube 70 mm wide which had a free space in its lower portion 200 mm high; thereover at intervals of 50 mm there were 40 wire screens each having an interval between meshes of 5 mm and there was provided about a free space having a height of 600 mm and a width of up to 160 mm.

There were led into the reactor in gaseous form in uniform flow hourly from below a gas mixture of 1500 normal liters (i.e., measured at standard temperature and pressure) of nitrogen and 2150 normal liters of ammonia and from the side there were led into the fluidized bed 130 mm above the bottom of the reactor a gaseous mixture of 1350 grams of acrolein, 1395 grams of acetone and 210 normal liters of nitrogen.

The reactor contained 2.0 kg of catalyst. The catalyst consisted of aluminum silicate containing 13% Al$_2$O$_3$, had a BET surface area of 500 cm$^2$/g, a pore volume of 0.75 cm$^3$/g, a pore diameter of 60$\times 10^{-8}$ cm (i.e., 60 A) and a particle size of 0.4 to 1.0 mm.

The temperature in the reactor was held at 440° C. The reaction mixture which left the reactor was free from acrolein. It was led at a temperature of 250° C. into a gas washing apparatus in which the pyridine compounds formed and the unreacted acetone was washed out. The remaining residual gas of ammonia and nitrogen after addition of 750 normal liters of ammonia hourly were recycled into the reactor.

The reaction of the acrolein was 100%, of the acetone 73%. There were produced hourly 550 grams of 2-methyl pyridine and 314 grams of 3-methyl pyridine, corresponding to yields of 25% and 28% based on the acrolein added (a total of 53% compared to Hargreave British Pat. No. 920,526 total yields of these 2 compounds of 33.5% in Example 1 and 37.4% in Example 2). Besides there were obtained 75 grams of pyridine and 55 grams of 2,6-dimethyl pyridine. There were recovered hourly 378 grams of acetone. Per kg of catalyst per hour the yield of 2-methyl pyridine and 3-methyl pyridine was 432 grams.

EXAMPLE 2

The procedure was the same as in Example 1 but there were fed in hourly 1680 grams of acrolein and 1045 grams of acetone. The reaction of the acrolein was 100%, of the acetone 75%. The yield of 2-methyl pyridine was 512 grams, corresponding to 18%; the yield of 3-methyl pyridine was 451 grams, corresponding to 32%, based on the acrolein added. Besides there were obtained 127 grams of pyridine and 39 grams of 2,6-dimethyl pyridine. Per kg of catalyst per hour the yield of 2-methyl pyridine and 3-methyl pyridine was 481 grams.

EXAMPLE 3

The procedure was the same as in Example 1 but there were fed in hourly 1010 grams of acrolein and 1740 grams of acetone and the reaction was carried out at 420° C. The acrolein was reacted 100%, the acetone 78%. The yield of 2-methyl pyridine was 470 grams, corresponding to 28%; the yield of 3-methyl pyridine 168 grams, corresponding to 20%, based on the acrolein added. Besides there were obtained 50 grams of pyridine and 30 grams of 2,6-dimethyl pyridine. Per kg of catalyst per hour the yield of 2-methyl pyridine and 3-methyl pyridine was 319 grams.

What is claimed is:

1. In a process for the production of 2-methyl pyridine and 3-methyl pyridine by the catalytic reaction of acrolein and acetone with ammonia in the gas phase the improvement comprising employing as the catalyst a highly dispersed aluminum silicate containing 3 to 30 weight percent aluminum oxide, a BET surface area of 200 to 800 m$^2$/g, a pore volume of 0.4 to 1.0 cm$^3$/g and a pore diameter of 20 to 100×10$^{-8}$ cm and wherein the catalyst is employed in a fluidized bed and the acrolein and acetone are introduced into the reactor separately from the ammonia.

2. A process according to claim 1 wherein the catalyst has an aluminum oxide content of 5 to 20 weight percent, a BET surface area of 300 to 600 m$^2$/g, a pore volume of 0.6 to 0.8 cm$^3$/g and a pore diameter of 40 to 80×10$^{-8}$ cm.

3. A process according to claim 2 wherein the aluminum oxide content is 10 to 15 weight percent.

4. A process according to claim 3 wherein per mole of acrolein there is employed 0.5 to 1.5 moles of acetone and per mole of total oxo compound 1.3 to 2.5 moles of ammonia.

5. A process according to claim 4 wherein there is also employed 1.0 to 2.5 moles of inert gas per mole of total oxo compound.

6. A process according to claim 2 wherein per mole of acrolein there is employed 0.5 to 1.5 mole of acetone and per mole of total oxo compound 1.3 to 2.5 moles of ammonia.

7. A process according to claim 6 wherein there is also employed 1.0 to 2.5 moles of inert gas per mole of total oxo compound.

8. A process according to claim 2 wherein per mole of acrolein there is employed 0.2 to 2.0 moles of acetone and per mole of total oxo compound 1.0 to 3.0 moles of ammonia.

9. A process according to claim 8 wherein there is also employed 0.5 to 3.0 moles of inert gas per mole of total oxo compound.

10. A process according to claim 1 wherein there is employed per mole of acrolein 0.5 to 1.5 moles of acetone.

11. A process according to claim 10 wherein there is employed per mole of total oxo compound 1.3 to 2.5 moles of ammonia.

12. A process according to claim 11 wherein there is also employed 1.0 to 2.5 moles of inert gas per mole of total oxo compound.

13. A process according to claim 1 wherein there is employed per mole of acrolein 0.2 to 2.0 moles of acetone and per mole of total oxo compound 1.0 to 3.0 moles of ammonia.

14. A process according to claim 13 wherein there is also employed 0.5 to 3.0 moles of inert gas per mole of total oxo compound.

15. A process according to claim 1 wherein there is employed per mole of acrolein 0.1 to 2.5 moles of acetone and at least 1 mole of ammonia per mole of total oxo compound.

16. A process according to claim 1 wherein the catalyst has a particle size of 0.1 to 3.0 mm.

17. A process according to claim 16 wherein the catalyst has a particle size of 0.2 to 2.0 mm.

18. A process according to claim 1 wherein the catalyst consists of said aluminum silicate.

19. A process according to claim 1 wherein the catalyst consists essentially of said aluminum silicate.